United States Patent [19]

Harwood-Nash et al.

[11] Patent Number: 4,616,814
[45] Date of Patent: Oct. 14, 1986

[54] X-RAY HEAD HOLDER

[75] Inventors: Derek C. Harwood-Nash, Willowdale; Charles R. Fitz, Toronto; Edward T. Zouch, Toronto; John M. Smith, Toronto, all of Canada

[73] Assignee: The Hospital for Sick Children, Toronto, Canada

[21] Appl. No.: 559,137

[22] Filed: Dec. 7, 1983

[51] Int. Cl.$^4$ ............................................. A61G 13/00
[52] U.S. Cl. ..................................... 269/328; 378/208
[58] Field of Search .......................... 269/64, 322–326, 269/328; 378/179, 208; 5/440, 434; 297/408; 403/161–163

[56] References Cited

U.S. PATENT DOCUMENTS 3,307,874  3/1967  Wilson ............................ 297/408 X
3,692,356  9/1972  Mertens .............................. 297/408
4,014,594  3/1977  Hain .................................... 297/408
4,045,678  8/1977  Rickard ......................... 269/328 X

FOREIGN PATENT DOCUMENTS 490867  2/1954  Italy ..................................... 269/324

Primary Examiner—Frederick R. Schmidt
Assistant Examiner—Steven P. Schad
Attorney, Agent, or Firm—Rogers, Bereskin & Parr

[57] ABSTRACT

A patient head holder is disclosed for use with a CT scanner and is suitable both for adult patients and for young children. The holder includes a support which is pivotable about a horizontal axis disposed below the region in which the neck of an adult patient would lie, and the attitude of the support can be adjusted incrementally over a wide range by means of two clutch assemblies.

15 Claims, 10 Drawing Figures

X-RAY HEAD HOLDER

This invention relates generally to X-ray and like apparatus used in hospitals to examine and/or treat patients, and is concerned more particularly with a device for supporting at least the head of a patient, during such examination and/or treatment.

This type of device is typically referred to in hospitals as an "X-Ray Head Holder" and this term will therefore be used in the following description, for the sake of convenience. The invention has, in fact, been devised primarily in connection with X-ray head holders for pediatric use in association with computerized tomography scanners (CT Scanners). Conventional X-ray head holders have a number of a significant disadvantages, and are generally unsatisfactory for pediatric use, particularly for premature newborns (whose weight may be as low as 700 grams). Normally, it is not practical to provide a special support for a child this small, and it is necessary to improvise by immobilizing the child on an adult head holder.

Typically, a conventional X-ray head holder may comprise a section of rigid plastic of approximately semi-cylindrical shape in which the patient's head is received. The plastic section is coupled to the X-ray table on which the patient lies by a pair of arcuate plates which slide in complimentary guides on a brackets secured to the table. This arrangement allows for limited adjustment of the angle of tilt of the head holder itself but does not allow for wide variations in the angular attitude of the head holder. In practice this can be a significant problem where X-rays are required to be taken with the head in different positions. For example, in some cases, it may be desirable to take an X-ray of the patient's head tilted forward with the chin on the chest, while in others, it may be desirable to tilt the head quite far back. These problems apply, not only to the examination and treatment of adult patients, but also in pediatrics, where the child is of the weight of above about 5 Kg. Below that weight the normal practice is to place the entire body of the child in the head holder and to immobilize the child, typically by using tape to secure it to the plastic support.

An object of the present invention is to provide an improved head holder, which, at least in accordance with the preferred embodiment described below, is particularly suitable both for pediatric use and with adult patients.

According to the invention, there is provided a device for supporting at least the head of a patient during X-ray examination and the like, comprising a support capable of carrying the head of an adult patient, a base adapted to be secured to external structure, and means coupling the support and base and adapted to permit pivotal movement to the support with respect to the base about an axis which normally extends generally horizontally and transversely below the neck area of an adult patient whose head is disposed on said support. The coupling means includes means for securing the support in an adjusted position about said axis. The support includes a lower portion which is intended to underlie the neck area of an adult patient and which curves generally about the axis defined by the coupling means, and an upper portion which extends generally tangentially outwardly from the lower portion and which is adapted to support the rear head area of an adult patient. The portions of the support have outer surfaces which merge together to present a substantially smooth profile to the patient. In use, the support can be adjusted about the said axis to provide for the required attitude of the head and the lower portion of the support represent a reasonably constant curved surface to the neck area of the patient.

It has been found in practice that an X-ray head holder of this form can be designed to provide for a wide range of angular adjustment of the attitude of the support about its axis, while at the same time presenting a substantially uniform and smooth exterior surface to the head and neck of the patient. For example, if the base of the head holder is secured to an end of the table of a CT scanner, it has been found possible to provide for a range of angular adjustment of the attitude of the support of about 135 degrees, say, from 60 degrees above the horizontal to 75 degrees below.

Preferably, the upper portion of the support is of uniformly, somewhat dished shape along its length. This shape has been found to be desirable in that it provides comfortable support with an adult patient while allowing a small child whose whole body is to be positioned on the support, to be securely held in place on the support.

Where the head holder is to be used in association with X-ray apparatus, the components of the holder should, as far as possible, be made of a radiolucent material so as to minimize interference with the X-ray image. In other cases, it might be desirable to use other materials. For example, the materials used in a head holder for an ultra-sound scanner would have to meet different criteria.

In any event, the means for securing the support in an adjusted position about said axis, should, of course, be designed to positively hold the support in an adjusted position with minimum risk of accidental dislodgement. In a preferred embodiment, this is accomplished by providing for inter-engaging series of teeth on the base and on a portion of the head holder which moves with the support, as will be more particularly described later.

In order that the invention may be more clearly understood, reference will now be made to the accompanying drawings which illustrates particular preferred embodiment of the invention by way of example, and in which.

Figure 5:
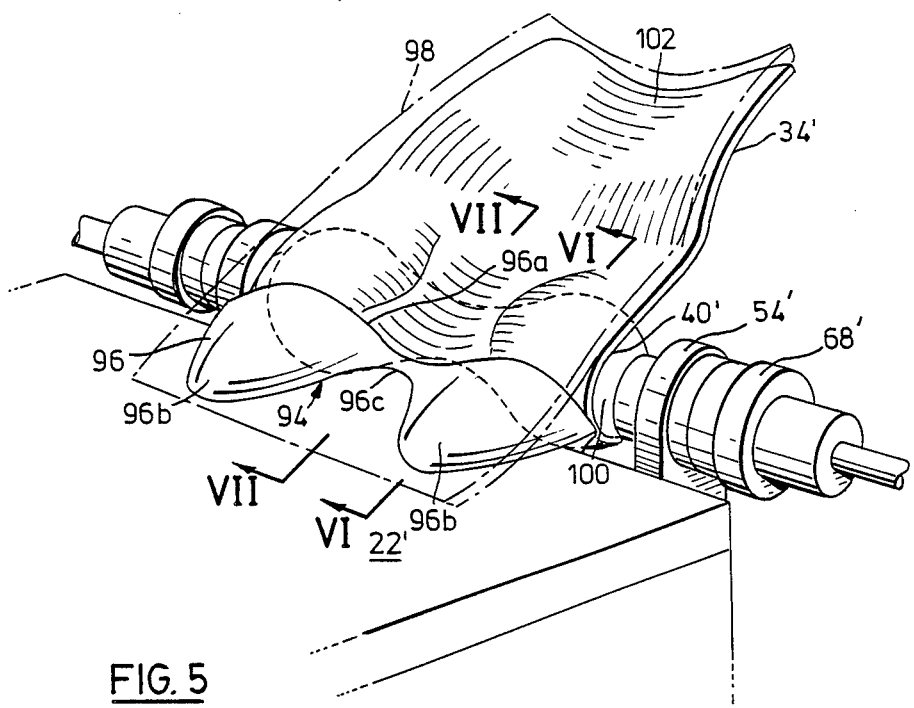
FIG. 5 is a perspective view similar to FIG. 1 showing a further feature of the invention.
Figure 7A:
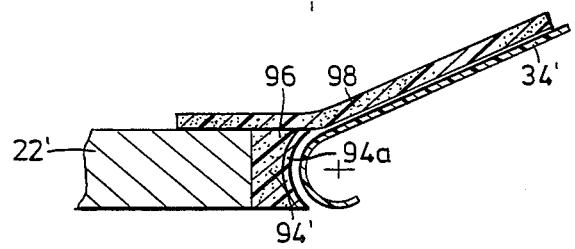
Figure 8:
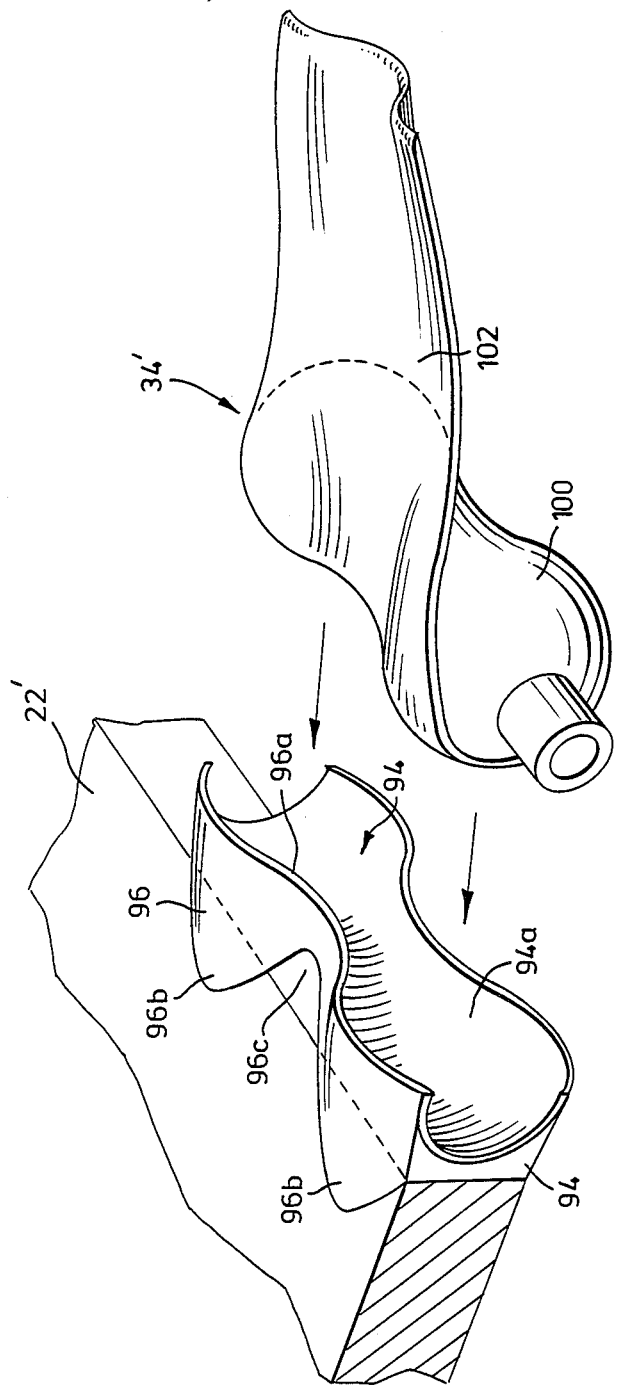

FIG. 7(a), (b) and (c) are sectional views on lines VII—VII of FIG. 5 showing the head holder in three different positions; and FIG. 8 is a rear perspective view, partly sectioned, showing the principal parts of FIG. 5 in exploded positions.

Figure 1:
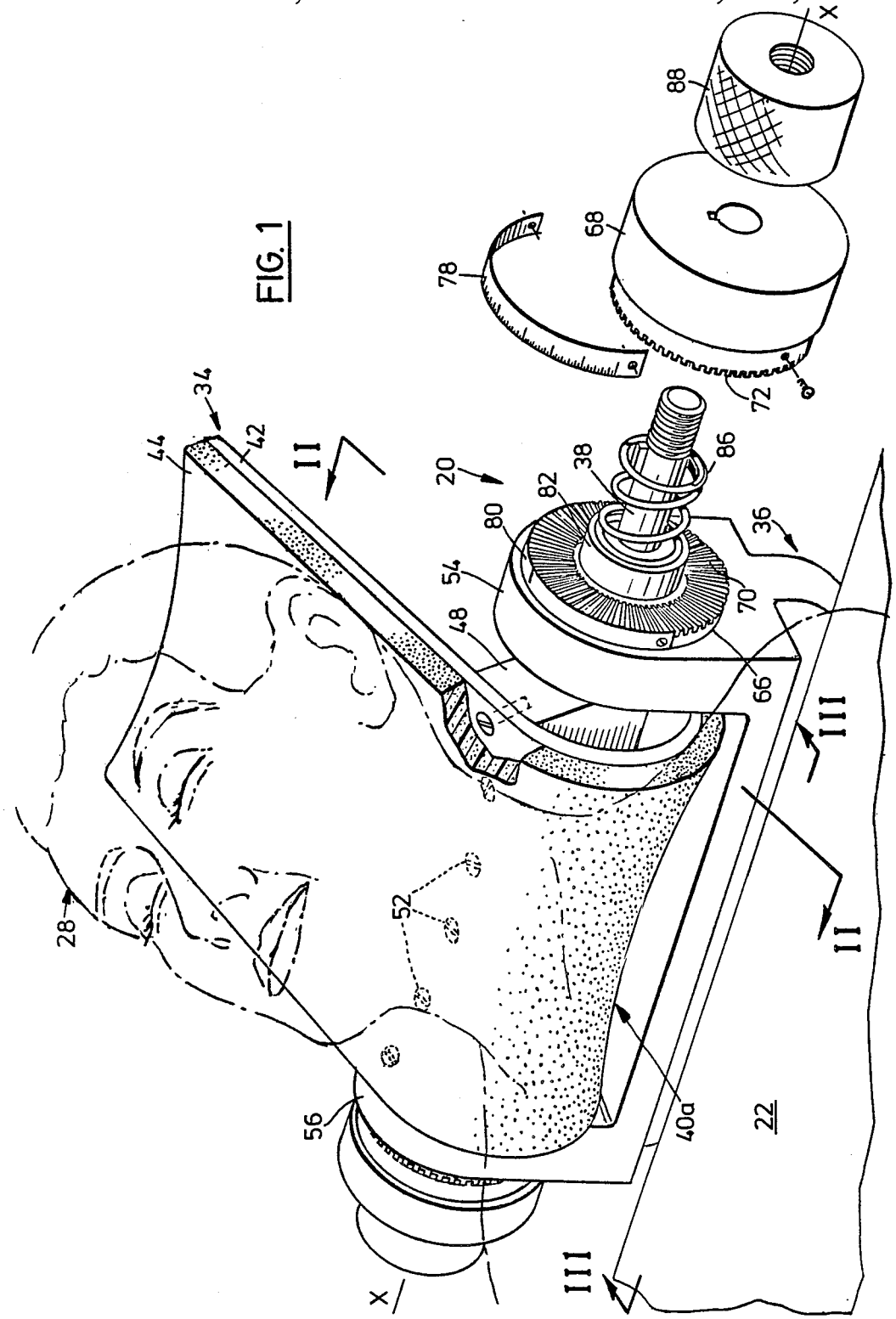
FIG. 1 is a perspective view of an X-ray head holder shown partly exploded.
Figure 2:
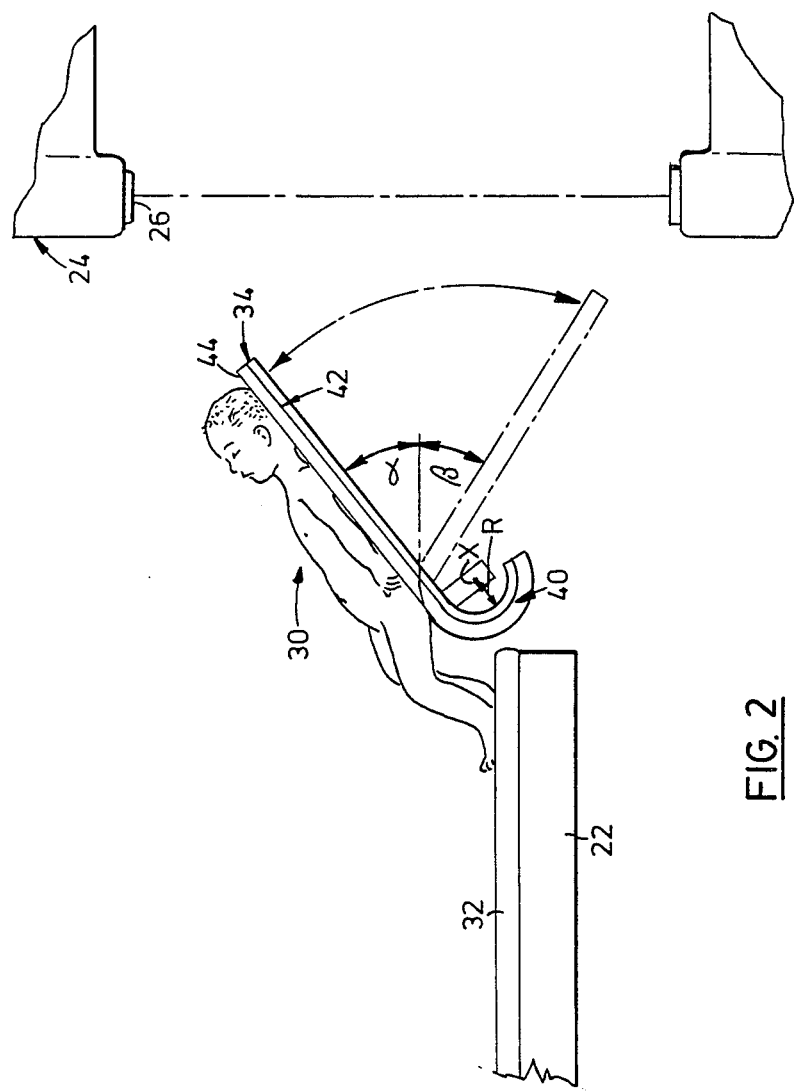
FIG. 2 is a somewhat diagrammatic sectional view generally on line II—II of FIG. 1 with supporting structure omitted.

Referring first to FIG. 1, the X-ray head holder is generally indicated by reference numeral 20 and is shown mounted on one end of a patient supporting table 22 for use in association with a CT scanner. In FIG. 2 part of the scanner is shown at 24 but the scanner itself forms no part of the invention and will therefore not be described in detail. It is sufficient to note that the scanner has an opening 26 into which the table 22 carrying the head holder 20 can be introduced for examination and/or treatment of a patient on the table. It will be understood from this that the head holder must be of relatively compact dimensions to be capable of entering opening 26.

FIG. 1 includes a representation in ghost outline at 28 of the head of an adult patient lying on table 22 with his or her head on the head holder 20. FIG. 2 illustrates at 30, how the whole body of a child can be supported on the same head holder. In that view, a mattress on table 22 is shown at 32.

Referring now to the head holder in more detail, its principal components are a support 34 which is capable of carrying the head of an adult patient, and a base 36 which in this embodiment is secured to the normal CAT scanner table 22 as will be described. The support 34 and base 36 are coupled together so that the support is pivotally movable with respect to the base about an axis X—X defined by a pivot shaft 38 which normally extends generally horizontally transversely and below the neck area of the patient 28. This allows the support 34 to pivot about axis X—X so that the attitude of the support can be varied according to the orientation of the patient required for the particular examination or treatment being performed. The support can be secured in an adjusted position about axis X—X by a locking arrangement to be described.

For the present, it is sufficient to note that the support 34 includes a lower portion 40 which is intended to underlie the neck area of the patient 28 and which curves generally about the axis X—X, as best seen in FIG. 2. The support also includes an upper portion 42 which extends generally tangentially outwardly from the lower portion 40 and which is adapted to support the rear head area of the patient. The two portions have respective outer surfaces which merge together and present a substantially smooth profile to the patient as can best be seen in FIG. 1. In that view, a foam cushioning pad is shown at 44 on the outer surface of support 34. The pad is also shown in FIG. 2. It will be seen from that view that, in the particular embodiment illustrated, the lower portion 40 in fact defines a constant radius, denoted R, in any plane generally normal to axis X—X. This means that the lower portion of the support will always present the same profile to the neck of the patient irrespective of the angular position of the support about axis X—X. In other words, the patient's neck will be equally well supported in any position of the support.

As can best be seen from FIG. 1, the lower portion 40 of the support is not in fact of constant cross-sectional shape throughout its length (along axis X—X) but is in fact "necked" somewhat in the region indicated by reference numeral 40a so that the profile presented to the neck is somewhat concave. That same concave profile is then continued along the upper portion 42 of the support so the support in fact provides a gently curved surface on which the patient's head can rest. At the same time, this configuration of support allows a small child to be readily secured on the support, for example, as shown in FIG. 2, by tapes. In fact, the rear surface of the upper portion 42 of the support is provided with three strips of VELCRO (TM) fabric denoted 46 which can be used to retain tapes or straps around the child or around the head of an adult patient; this is conventional practice with existing head holders.

In this embodiment, the support 34 is moulded in one piece in a polycarbonate plastic material. This material is radio-lucent and will not affect X-ray photographs taken using the head holder. However, other appropriate radio-lucent materials can of course be used. It should also be noted that this stage that, although the support 34 is shown as having been formed in one piece, this is not of course essential. Formation of the support 34 as shown requires special moulds because of the compound curvatures involved in the area of the lower portion 40 and for the sake of manufacturing expediency, it may be more convenient to make the upper and lower portions of the support separately and secure them together, for example by adhesive or by mechanical fasteners such as screws. In an alternative embodiment, the lower portion 40 of the support could in fact be in the form of a generally channel-shaped section positioned to curve about axis X—X. In that event, if the upper portion 42 of the support is to be curved as shown, one wall of the channel would preferably be cuved to conform with the curvature of the upper portion and that curved wall of the channel would then be secured to a separate component forming the upper portion 42.

Support 34 is carried on shaft 38 by way of a mounting block 48 which is secured to the underside of support 34 approximately in the vicinity of the lower end of the upper portion 42 of the support. Shaft 38 extends through the mounting block 48 and is clamped onto the block by three screws shown at 50 in FIG. 4 so that the shaft 38 turns with the mounting block 48. As shown in the drawings, the support is in turn secured to the mounting block by a series of screws 52 (FIG. 1) which extend through the support and into the mounting block. In an alternative embodiment, the block could of course be secured to the support by adhesive. This would have the advantage of avoiding any interference to the X-ray pattern caused by screws 52. In this embodiment, the block itself is made of NYLON (TM), which is a radio-lucent material.

Figure 3:
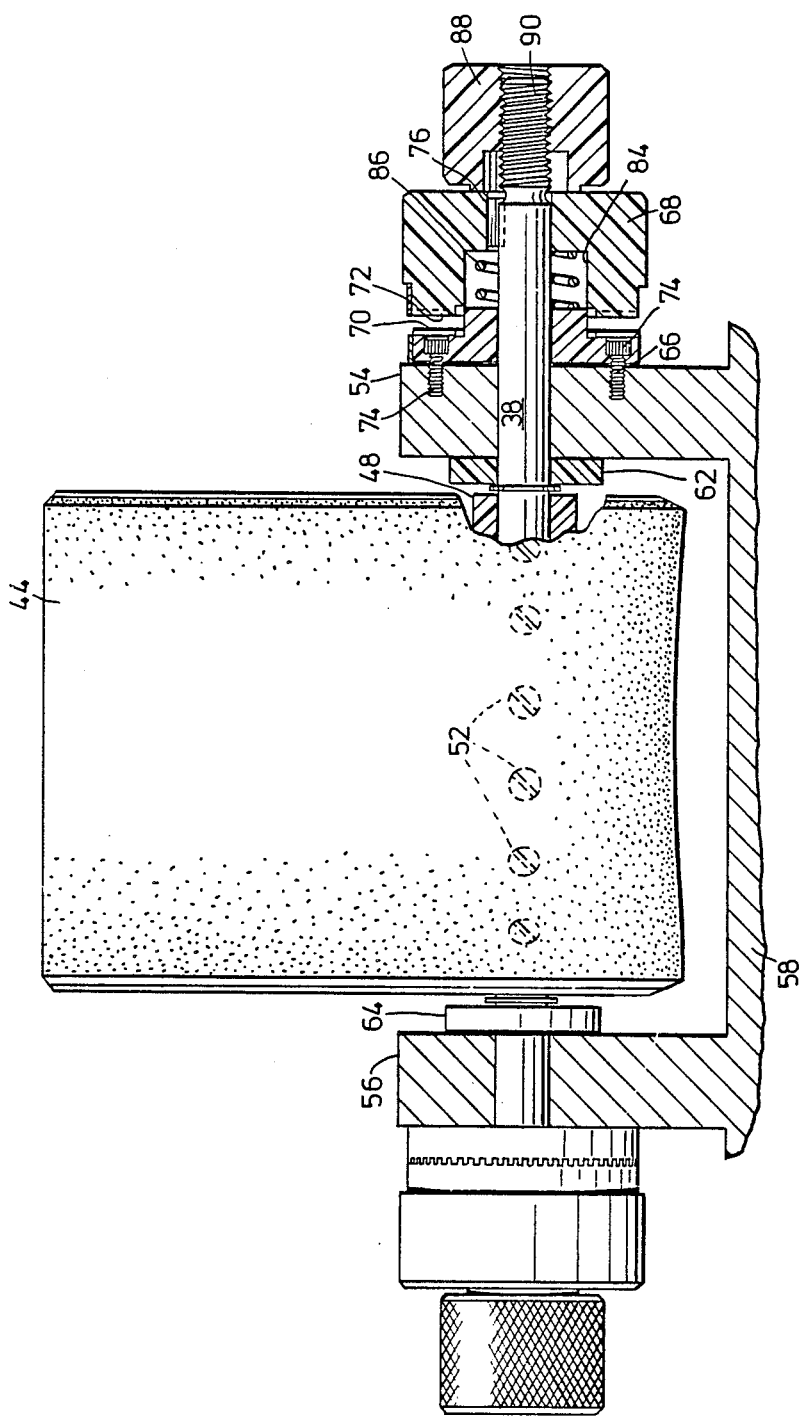
FIG. 3 is a sectional view on line III—III of FIG. 1.
Figure 4:
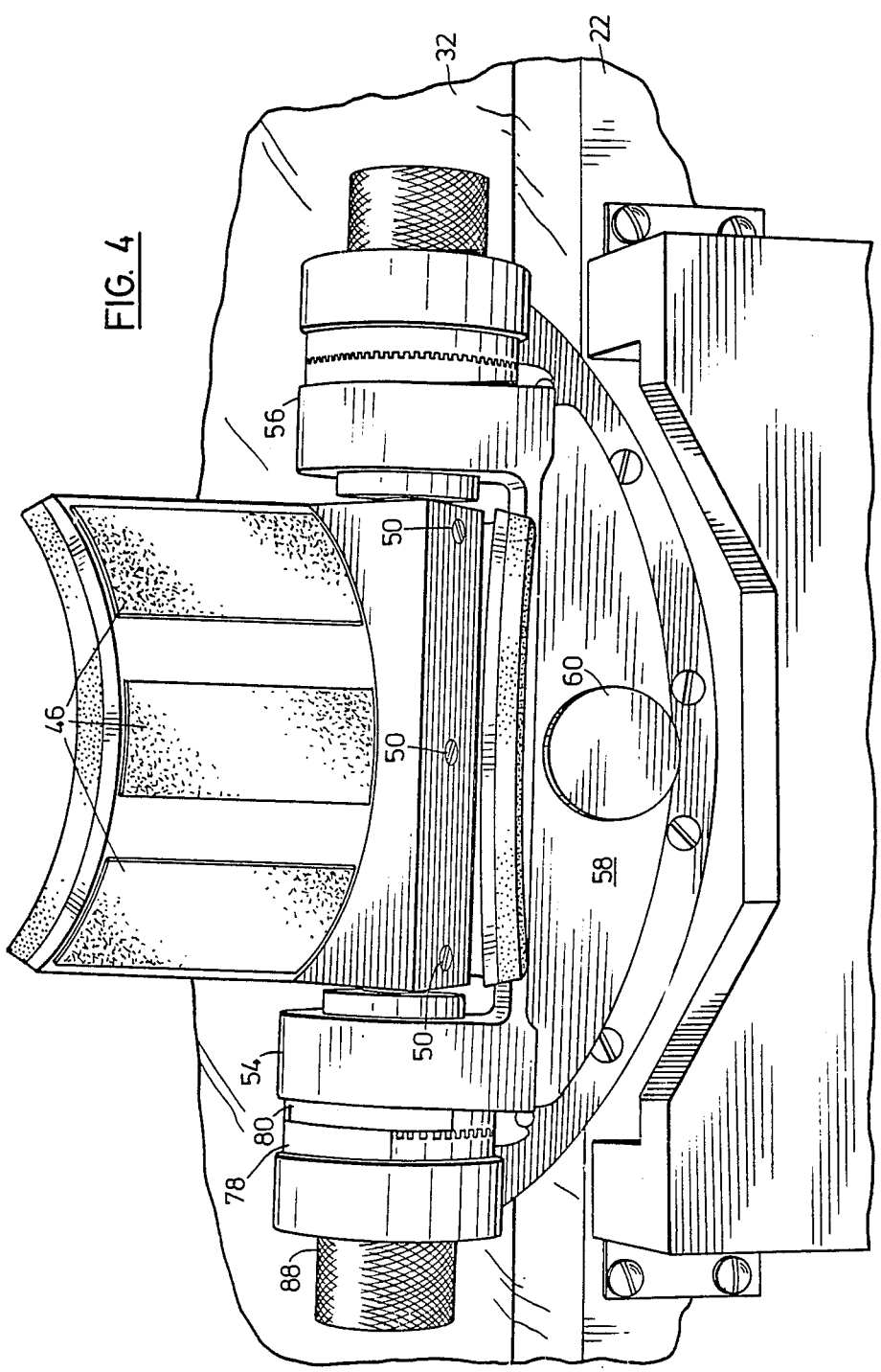
FIG. 4 is a rear perspective view corresponding to FIG. 1.

Base 36 includes two upstanding lugs 54 and 56 disposed adjacent and outwardly of respectively opposite sides of the support 34 and the shaft 38 passes through bores in the respective lugs as best shown in FIG. 3. FIG. 4 shows the base as seen from the opposite side compared with FIG. 1 and it will be seen that the main body of the base, denoted 58, is of part circular shape and is coupled to the relevant end face of the table 22 by a pivot 60 which allows limited lateral tilting of the head holder about a longitudinal axis of table 22, as is normal in conventional head holders. In this embodiment, the entire base including the lugs 54 and 56 is made in one piece in metal. This has the obvious disadvantage that the metal is not radioluscent but in practice this does not represent a problem because the base is normally outside the range of "view" of the X-ray scanner.

Referring now to FIG. 3, it will be remembered that shaft 38 will turn in the lugs 54 and 56 as the attitude of the support 34 about axis X—X is adjusted in practice. Washers generally indicated at 62 and 64 are provided between the lugs 54 and 56 respectively and the mounting block 48 to ensure smooth pivotal movement of the support. Externally of the two lugs, shaft 38 is provided at both ends with means for locking the shaft 38 in any one of a series of angularly spaced positions corresponding to different inclinations of support 34. In this embodiment, locking means are provided at both ends of shaft 38 for added security; however, it may of course be sufficient to provide locking means at one end of shaft 38 only. The two locking means are essentially the same and the following description will therefore be made with reference only to the locking means shown at the right-hand end of shaft 38 in FIG. 3.

The locking means takes the form of a clutch-like arrangement comprising a pair of collars having abutting faces formed with respective series of inter-engageable teeth which can be disengaged by moving the collars apart. As seen in FIG. 3, the two collars are denoted respectively 66 and 68 and carry respective series of teeth 70 and 72. Collar 66 is secured by bolts 74 to the outer face of the base lug 54 while collar 68 is keyed to shaft 38 by an axially extending key 76 on the shaft which engages in a complimentary keyway in collar 68.

The two collars are shown in exploded positions in FIG. 1 and the teeth 70 on collar 66 are shown exposed. It will be seen that the teeth are uniform and extend radially outwardly from axis X—X. Teeth 72 on the other collar are of course complimentary. In this particular embodiment, the pitch of the respective series of teeth is selected to correspond to incremental movements of 5° of arc of support 34 about axis X—X. In other words, by disengaging the two collars and moving collar 68 (and with it shaft 38) to the extent of one tooth in either direction, the inclination of support 34 will be changed by 5°. As best seen in FIG. 4, the corresponding outer collar 68 at the opposite side of the head holder is provided with a graduated scale 78 which co-operates with a fixed mark on the other collar. The scale is graduated to indicate the inclination of support 34.

Referring back to FIG. 1, it will be seen that collar 66 includes an integral extension 82 at its center which is received in a complimentary recess 84 in collar 68 (see FIG. 3). This recess also receives a helical compression spring 86 arranged to normally bias the two collars 66 and 68 apart. The two collars 66 and 68 can be brought into co-operating relationship against the biassing effect of spring 86 by a knurled knob 88 which is threaded onto a screw-threaded outer portion 90 of shaft 38. Thus, by tightening knob 88, collar 68 is displaced towards collar 66 against the biassing effect of spring 86 until its teeth 72 engage in the teeth 70 of collar 66. The respective sets of teeth are provided with an appropriate "lead" to facilitate such engagement. Conversely, when knob 88 is loosened, the spring 86 will automatically separate the collars 66 and 68, freeing the shaft 38 (assuming that the collars at the opposite end of the shaft have also been released).

The described embodiment has the advantage that in practice, the attitude of the head holder can readily be adjusted by simultaneously loosening the two knurled knobs (as knob 88) while gripping the adjacent collars keyed to shaft 38. When the two sets of teeth at both sides of the head holder have just disengaged, the collars can be turned to turn shaft 38 and bring the support 34 to the required orientation as indicated by a graduated scale 78 (FIG. 4). That position can then be temporarily held by tightening one or both of the knurled knobs. Fine adjustments in increments of 5° are then possible until the exact required position has been found. The two knobs, as knob 88, are then finally tightened to positively lock the head holder in the required position.

As has been indicated previously, it has been found possible to adjust the attitude of the head holder over at least a range of adjustment of 135° from an inclination of 60° above the horizontal (indicated by angle α in FIG. 2) to 75° below the horizontal (indicated by the angle β). This is well within the normal range of adjustments required in practice and in fact may even be exceeded by the form of head holder as shown in the drawings.

With the exception of shaft 38, spring 86 and screws 52, the components used to lock shaft 38 are all made of nylon and in practice, the remaining components are generally outside the range of view of the X-ray scanner.

Reference will now be made to FIGS. 5 to 8 in describing further features of the invention. In those views, primed reference numerals will be used to denote parts which correspond with parts shown in previous views.

FIG. 5 is a view generally similar to FIG. 1 and shows a head holder 20' similar to the head holder of FIG. 1 (but shown without the foam pad 44 of FIG. 1). The head holder support 34' is profiled somewhat differently in the FIG. 5 embodiment in that the side margins of the lower portion 40' of the support curve downwardly (towards axis X—X), giving portion 40' a generally dumbbell shape overall. Along the upper portion 42' the side margins of the support curve progressively upwardly to provide a cradle shape for the patients' head. This support profile is believed to be desirable in terms of patient comfort and safety. The head holder is in fact formed by a dumbbell-shaped core 100 to which a shaped rigid plastic sheet 102 is secured. The head holder is shown mounted on one end of a table 22' which has an upper surface denoted 92. Compared with FIG. 1 the table is higher with respect to the head holder; as can best be seen from FIG. 7, surface 92 is generally even with the top surface of support 34' in the region of its centre. Surface 92 will normally be defined by the top surface of a cushioning pad or mattress supported on a rigid table top (not shown).

An intermediate supporting element denoted 94 is disposed between the head holder 20' and the table upper surface 92 and has an outer surface 96 which extends between the upper surface of the table and the outer surfaces of the support 34' of the head holder. Surface 96 is shaped to provide a smooth transition between the head holder 20' and the table 22' so that the substantially smooth profile presented to the patient by the head holder is continued to the table and provides substanital continuity of support for a patient. A foam cushioning pad is indicated at ghost outline at 98 in FIG. 5 and is shaped to be laid over support 34' (in place of the cushioning pad 44 of FIG. 1) and to extend down over element 94 and onto the upper surface of table 22'. This form of pad has the advantage that it not only provides a cushioned surface but also covers the junction between element 94 and the head holder itself so that there is no risk that the patient can become trapped. However, in an alternative embodiment, element 94 could in principle be used directly with a head holder having its own cushioning pad as shown in FIG. 1.

The intermediate supporting element 94 extends slightly beyond the ends of support 34' as shown and is contoured so that its upper surface 96 matches the contour of the lower portion 40' at the upper marginal portion 96a of the surface 96 and then merges smoothly to marginal portions 96b where the element meets table surface 92. Intermediate portions 96b element 94 is shaped to define a recess 96c for receiving the patient's lower neck area. Contouring the element 94 in this way ensures the smooth transition referred to above but, again, is not essential. The leading face 94a of element 94 (the face closest to the head holder) is also contoured to match the contour of support 34' as best seen in FIG. 8, but again this is not essential. The primary criterion should be that the upper marginal portion 96a of surface 96 should be maintained as close as possible to the outer surface of the support at all angular positions of the head holder.

Figure 6:
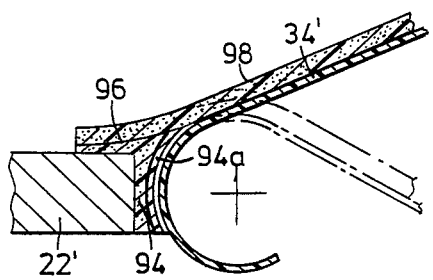
FIG. 6 is a diagrammatic sectional view on line VI—VI of FIG. 5.
Figure 7B:
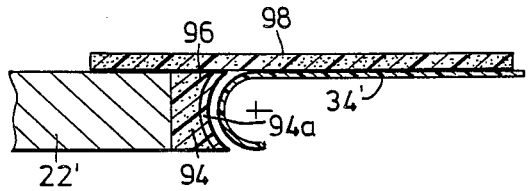
Figure 7C:
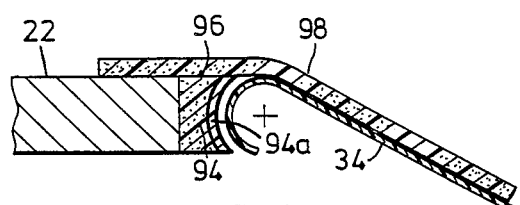

A comparison of FIGS. 6 and 7 will serve to illustrate the contours of the surfaces 96 and 94a of element 94. Thus, FIG. 6 is a sectional view taken adjacent one end of element 94 at a position at which the element is of approximately its maximum height while FIG. 7 is taken generally at the center of the width of the element. FIG. 7 in fact comprises three views denoted (a), (b) and (c) are show, respectively, the head holder in three different angular orientations with respect to axis X—X. In FIG. 6, the head holder is shown oriented generally as shown in FIG. 7(a) while the ghost outline profile shown in FIG. 6 corresponds to the reclined position shown in FIG. 7(c).

FIGS. 6 and 7 illustrate in quite graphic fashion the manner in which the head holder, intermediate support element 94 and table 22' operate collectively as a patient supporting "system" which provides a smooth profile to the patient in substantially all orientations of the head holder.

Element 94 itself may be manufactured in various ways but preferably is made of an at least partly resilient plastic material. The element may be free standing on table 22' or may be positively secured to the table, e.g. by adhesive or fasteners. In the illustrated embodiment, the element is secured to the relevant end face of the table.

It will of course be understood that the preceding description relates to a particular preferred embodiment of the invention only and that many modifications are possible in addition to those which have been indicated previously. For example, an attachment generally similar to attachment 94 (FIG. 5) could of course be used with other forms of head holder than that specifically shown. Also, the attachment could be used where the table is at a lower height than that shown in FIG. 5, in which case the attachment would probably be more wedge shaped.

We claim:

1. A device for supporting at least the head of a patient during x-ray examination and the like, the device comprising:
   a support capable of carrying the head of an adult patient;
   a base adapted to be secured to external structure and defining two upstanding lugs on respectively opposite sides of said support; and,
   means coupling the support and base and adapted to permit pivotal movement of the support with respect to the base about an axis which normally extends generally horizontally transversely of and below the neck area of an adult patient whose head is disposed on said support, said coupling means including: a shaft coupled to the support and extending through openings in said lugs in which the shaft can turn as the attitude of the support is adjusted; and means for securing the support in an adjusted position about said axis, comprising: first and second collars adapted to be releasably locked together in any of a series of angularly spaced positions of said shaft, one of said collars being secured to said base and the other collar being keyed to the shaft for longitudinal sliding movement therealong between a first position in which said collars are disengaged, and a second position, in which said collars are releasably locked together;
   said support including a lower portion which is intended to underlie the neck area of said patient and which curves generally about the axis defined by said coupling means, and an upper portion which extends generally tangentially outwardly from said lower portion and which is adapted to support the rear head area of an adult patient, said portions defining respective outer surfaces which merge together to present a substantially smooth profile to the patient;
   whereby the support can be adjusted to a variety of angular positions about said axis, in any of which said outer surfaces provide substantially continuous support for the head and neck area of the patient.

2. A device as claimed in claim 1 wherein said lower portion of the support is shaped so that, in any plane extending transversely through said axis, all points on the outer surface of said portion are equidistant from said axis, whereby said lower portion of said support presents a substantially constant profile to the patient as the support is adjusted angularly about said axis.

3. A device as claimed in claim 2, wherein said lower portion of the support is smoothly contoured to define a centre region of less diameter than regions of said portion considered in the direction of said axis, and wherein the profile of said portion is continued into said upper portion of the support whereby the support presents a generally concave outer surface to the head and neck area of a patient.

4. A device as claimed in claim 1, wherein said collars define respective opposed faces formed with respective series of teeth extending radially of said axis, the teeth in said respective series being engageable with one another in any of a series of angularly spaced position of said shaft.

5. A device as claimed in claim 4, wherein the pitch of the teeth in said series is selected to correspond a 5 degree increment in the angular orientation of said support about said axis.

6. A device as claimed in claim 4, wherein said collars are spring biased towards said disengaged position, and wherein said movable collar can be displaced to bring said collars into said engagement by an actuator element screw-threaded to said shaft and manually operable from externally of the device to urge said collars into engagement.

7. A device as claimed in claim 1 wherein respective sets of clutch members are provided on said shaft adjacent to and outwardly of each of said lugs.

8. A device as claimed in claim 1 wherein said support comprises a one-piece moulding in a radio-lucent plastic material.

9. A device as claimed in claim 1, wherein said outer surface of the support is covered with a cushioning layer of resilient material.

10. The combination of a device as claimed in claim 1, a table to which said device is coupled, and an intermediate supporting element disposed between said device and the table, said element having an outer surface which extends between the table upper surface and the outer surfaces of the support of said device and which is shaped to provide a smooth transition between the device and table, whereby said substantially smooth profile presented to the patient is continued to the table surface and provide substantial continuity of support for the patient.

11. The combination as claimed in claim 10, wherein the lower portion of the support of said device is smoothly contoured to define a center region of a minimum diameter and outer regions of greater diameter defining a generally concave profile, and wherein said profile is continued into said upper portion of the support whereby the support presents a generally concave outer surface to the head and neck area of a patient, and wherein said outer surface of the intermediate supporting element includes first and second end portions adjacent said device and table surface respectively, said first end portion being shaped to conform with said generally concave profile, and said element outer surface merging smoothly between said first and second end portions.

12. The combination as claimed in claim 10, wherein said supporting element defines a leading end face adjacent said support of the device which face is contoured to correspond to the contour of said lower portion of the support.

13. A combination as claimed in claim 10, further comprising a single resilient cushioning pad covering said outer surfaces of the support and intermediate supporting element.

14. A combination as claimed in claim 10, wherein said intermediate supporting element is a resilient plastic moulding.

15. A combination as claimed in claim 10, wherein said intermediate supporting element is secured to the table.

* * * * *